United States Patent
Miki et al.

(10) Patent No.: US 10,603,178 B2
(45) Date of Patent: Mar. 31, 2020

(54) PROSTHETIC HIP SYSTEM

(71) Applicant: Storge Enterprises, LLC, Pinecrest, FL (US)

(72) Inventors: Roberto Augusto Miki, Pinecrest, FL (US); Ernesto Hernandez, Weston, FL (US); Javier E. Castaneda, Miami, FL (US); John William Box, Coral Gables, FL (US); Scott M. Whitten, Sunrise, FL (US)

(73) Assignee: Storage Enterprises, LLC, Pinecrest, FL (US)

( * ) Notice: Subject to any disclaimer, the term of this patent is extended or adjusted under 35 U.S.C. 154(b) by 128 days.

(21) Appl. No.: 15/820,271

(22) Filed: Nov. 21, 2017

(65) Prior Publication Data

US 2018/0153699 A1 Jun. 7, 2018

Related U.S. Application Data

(60) Provisional application No. 62/425,463, filed on Nov. 22, 2016.

(51) Int. Cl.
*A61F 2/32* (2006.01)
*A61F 2/34* (2006.01)
(Continued)

(52) U.S. Cl.
CPC ............ *A61F 2/34* (2013.01); *A61B 17/1666* (2013.01); *A61B 17/1668* (2013.01);
(Continued)

(58) Field of Classification Search
CPC ...... A61F 2002/3416; A61F 2002/3425; A61F 2/30771; A61F 2002/2828;
(Continued)

(56) References Cited

U.S. PATENT DOCUMENTS

| 4,123,806 A | 11/1978 | Amstutz et al. |
| 4,173,797 A | 11/1979 | Langlais et al. |

(Continued)

FOREIGN PATENT DOCUMENTS

| DE | 2807289 A1 | 8/1979 |
| JP | 2013-524981 A | 6/2013 |

*Primary Examiner* — Thomas Sweet
*Assistant Examiner* — Rebecca Lynee Zimmerman
(74) *Attorney, Agent, or Firm* — Gordon & Jacobson, P.C.

(57) ABSTRACT

An implantable prosthetic hip system generally includes acetabular components, femoral components, and tooling for implanting the components. The acetabular components include an acetabular socket and a bushing received within the acetabular socket. The acetabular socket defines a reamer with cutters for preparing the acetabulum. The femoral components generally include a cutter cap, a head cover, and a screw. Tooling includes a cutting bit that is used to cut a flat on the femoral head. The cutter cap is advanced in a cutting action onto the femoral head to remove the sides of the head and the cutter cap is also implanted on the femoral head. The head cover is positioned on the cutter cap, and retained with a coupling screw. The acetabular socket and the head cover are assembled with a bushing therebetween. Methods of implantation are also provided.

39 Claims, 17 Drawing Sheets

(51) Int. Cl.
*A61F 2/30* (2006.01)
*A61F 2/46* (2006.01)
*A61B 17/16* (2006.01)
*A61F 2/36* (2006.01)

(52) U.S. Cl.
CPC ........ *A61F 2/30771* (2013.01); *A61F 2/3601* (2013.01); *A61F 2/4607* (2013.01); *A61F 2002/3093* (2013.01); *A61F 2002/30205* (2013.01); *A61F 2002/30247* (2013.01); *A61F 2002/30377* (2013.01); *A61F 2002/30405* (2013.01); *A61F 2002/30433* (2013.01); *A61F 2002/30774* (2013.01); *A61F 2002/30784* (2013.01); *A61F 2002/30904* (2013.01); *A61F 2002/3401* (2013.01); *A61F 2002/3419* (2013.01); *A61F 2002/3429* (2013.01); *A61F 2002/4681* (2013.01)

(58) Field of Classification Search
CPC ...... A61F 2002/2825; A61F 2002/3617; A61F 2002/368; A61F 2/36; A61F 2/367; A61F 2002/3684; A61F 2/4607; A61F 2002/30205; A61F 2002/30247; A61F 2002/30904; A61F 2/4684; A61F 2002/3411; A61F 2002/3603; A61B 17/175; A61B 17/1668; A61B 17/1666; A61B 17/155; A61B 17/144; A61B 17/142; A61B 17/147; A61B 17/1614; A61B 17/16

See application file for complete search history.

(56) References Cited

U.S. PATENT DOCUMENTS

| | | |
|---|---|---|
| 4,846,841 A | 7/1989 | Oh |
| 5,258,033 A | 11/1993 | Lawes et al. |
| 6,156,069 A | 12/2000 | Amstutz |
| 6,379,389 B1* | 4/2002 | Koch ................ A61F 2/34 623/22.15 |
| 8,152,855 B2 | 4/2012 | Tulkis et al. |
| 8,317,871 B2 | 11/2012 | Stone et al. |
| 8,834,479 B2 | 9/2014 | Aux Epaules et al. |
| 8,945,233 B2 | 2/2015 | Forsell |
| 9,138,258 B2 | 9/2015 | Geebelen |
| 2003/0130741 A1* | 7/2003 | McMinn ............ A61B 17/15 623/23.14 |
| 2005/0085915 A1* | 4/2005 | Steinberg ........ A61B 17/1666 623/17.16 |
| 2008/0004710 A1 | 1/2008 | Ledger et al. |
| 2008/0262626 A1 | 10/2008 | Raugel |
| 2009/0248170 A1* | 10/2009 | Tuke ................ A61B 17/175 623/23.11 |
| 2010/0191344 A1 | 7/2010 | Grundei et al. |
| 2014/0316531 A1 | 10/2014 | Klinger et al. |
| 2016/0089156 A1* | 3/2016 | Fortin ............ A61B 17/1666 606/81 |

* cited by examiner

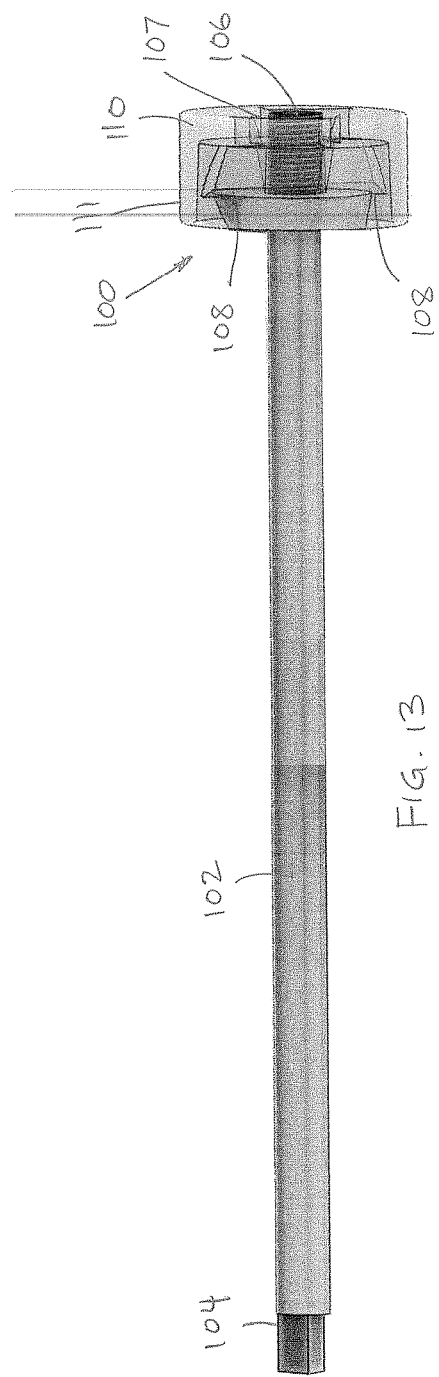
FIG. 13
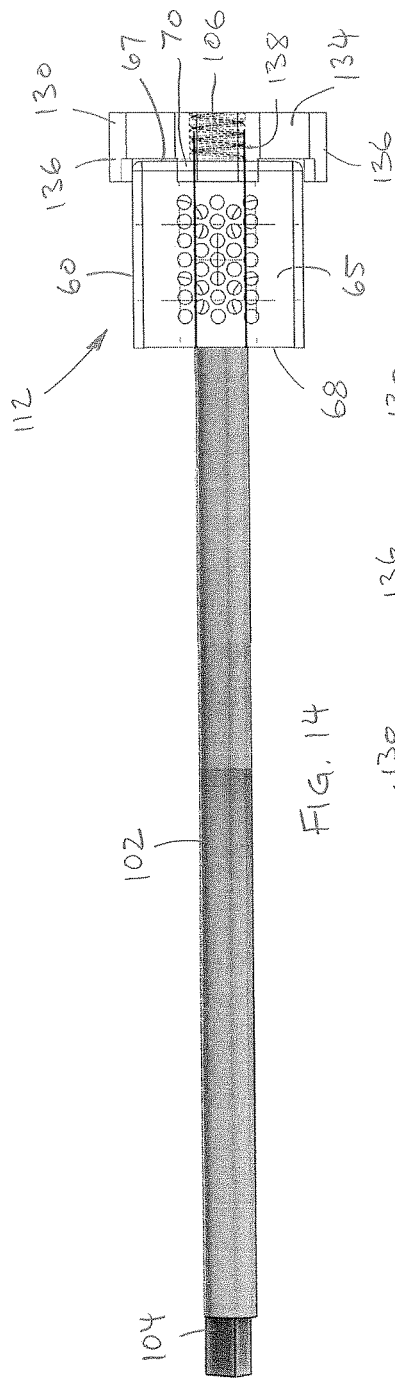
FIG. 14
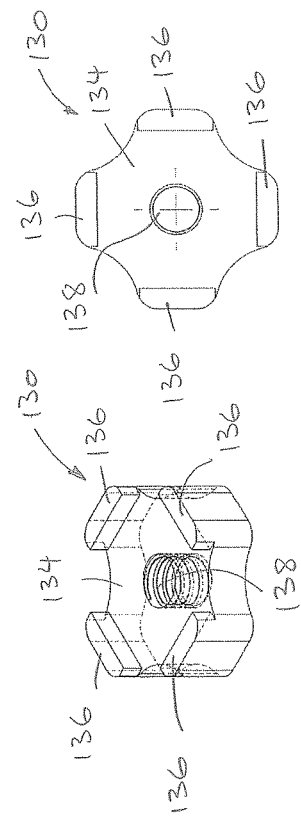
FIG. 15
FIG. 16

PROSTHETIC HIP SYSTEM

CROSS-REFERENCE TO RELATED APPLICATION

This application claims benefit to U.S. Prov. Ser. No. 62/425,463, filed Nov. 22, 2016, which is hereby incorporated by reference herein in its entirety.

BACKGROUND

1. Field

The present invention relates to implantable prostheses. More particularly, the invention relates to hip prostheses, and methods, systems and tools for the implantation of hip prostheses.

2. State of the Art

Artificial joint prostheses are widely used today, restoring joint mobility to patients afflicted by a variety of conditions, including degeneration of the joint and bone structure. Typically, the failed bone structure is replaced with an orthopedic implant that mimics, as closely as possible, the function of the natural anatomy.

Requirements for the useful life of a prosthetic implant continue to grow with the increase in human life expectancy. Also, as implants improve, younger patients are considered as candidates for implants. It is therefore desirable to develop implants that, while durable in their own right, minimize the difficulty of replacement.

The strength and longevity of implants in large part depend on interfaces: the bone/implant interface as well as the implant/implant articulating interface. For example, an anatomical hip joint is a ball-in-socket joint, and includes a rounded femoral head and a cup-like socket (acetabular cup) formed in the pelvis. The surfaces of the rounded femoral head and the acetabular cup continually wear against each other as a person walks. The abrasion, along with normal loading, creates stress on the hip joint and adjacent bones. If the femoral head or the acetabular cup is replaced with an implant, this stress is ideally well tolerated by the implant's bearing surfaces to prevent premature implant failure.

Nevertheless, with prior art hip implants, replacement of at least a portion of the implant often has been required. Prior art designs often require the entire implant to be replaced even if only a portion of the implant fails. Similarly, the entire implant may have to be replaced if the implant is intact but certain conditions surrounding the implant have changed. This is often due to the implant suffering from a decrease in support from the adjacent bone due to stress shielding or other negative effects of the implant on surrounding bone.

Surgeons have sought a more conservative device than an implant using an intramedullary stem as part of the femoral prosthesis. There have been a number of attempts at implants using short stems or femoral caps without stems and requiring less extensive surgery. This type of prosthesis is generally known as a hip resurfacing prosthesis. In the mid-1940's, Judet in France designed a prosthesis whereby the majority of the femoral head was removed and a replacement device was fitted with a peg or nail which passed a short way down the femoral neck. Small movement of the device against the bone caused friction of the bone and the bending loads on the peg often caused them to break out underneath the bony femoral neck. In the mid-1970's, double cup type arthroplasty was tried. There were several designs: Wagner in Germany, an Italian Group, Imperial College London and the Tharies design from Amstutz in California.

These all removed a fair proportion of the femoral bearing surface by turning it down to a cylindrical form or hemispherical form. A metal shell was then fixed with bone cement on the remaining bony peg. The acetabular cup was conventional. Unlike normal total hips, however, which have standard femoral head sizes in the range of 22-32 mm, these double cup arthroplasties have large bearing surface diameters closer to the original hip, typically in a range from 40-60 mm. These latter double cup designs commonly failed either by a crack progressing around the bone cement between the prosthetic femoral shell and the bone or by a fracture of the bone across from one side of the prosthetic femoral component rim to the other.

Current approaches to femoral head resurfacing can be traced back to Amstutz in U.S. Pat. No. 4,123,806. In the '806 patent, a hemispherical cap is cemented to a prepared femoral head while preserving a substantial portion of the femoral head. In U.S. Pat. No. 6,156,069, Amstutz shows a femoral head resurfacing implant having a stem. A similar femoral head resurfacing technique having a stem called Birmingham Hip Resurfacing has been developed by McMinn in the United Kingdom.

These stem-type femoral head resurfacing prostheses consist of a bearing cap provided with a central pin that guides the prosthesis during the insertion. The guiding is important because it ensures that the prosthesis will be seating at the appropriate orientation planned by the surgeon with regard to the bone. A consequence of the misalignment of the prosthesis is a sub-optimal load transfer to the bone that can lead to the failure of the prosthetic joint. Similar to the problems with the prostheses having a stem extending into the femoral shaft, a stem-type resurfacing prostheses requires the surgeon to remove enough bone in the neck of the femur so that it can host the pin of the prosthesis and the stem can contribute to stress shielding. Therefore the stem-type prosthesis is not as bone preserving as a stemless prosthesis, either in the short term or long term.

Notwithstanding the problem of guiding a stemless prosthesis, stemless approaches have been advocated and continue to be developed. A modular approach to a stemless femoral hip resurfacing is shown in U.S. Pat. No. 4,846,841 to Oh. In this approach, a frustroconical cap is press-fit to a prepared femoral head. A ball component is then attached to and retained by the cap using a Morse taper fit. A similar approach is shown in U.S. Pat. No. 5,258,033 to Lawes and Ling, which shows a ball component cemented either directly to a prepared head or, additionally, retained by a press-fit with a frustroconical cap. Another approach to stemless femoral head resurfacing is described in U.S. Pub. No. 20080004710, entitled Femoral Head Resurfacing.

All of these more modern hip resurfacing approaches require that the femoral head be prepared to provide a properly oriented and shaped bone interface for the implant by shaping the head. The outer prepared bone interface with the implant is symmetrical around a prepared head axis passing through and established with reference to the central region of the femoral neck and is typically cylindrical or conical but may be a more complex tapering solid of revolution. The proximal portion of the prepared head can be a flat surface, tapered, domed, chamfered, or any combination of these features and is usually performed as a separate resection. If a stem is used, it may be cylindrical, conical or a more complex tapering solid of revolution and is typically short compared to a conventional intramedullary stem. The portion of the bone that hosts the prosthesis must be shaped so that it matches the shape of the prosthesis. The size and shape of the bone may fit exactly the shape and size of the prosthesis or may provide room for cementing to take place or have an excess of bone in a region to allow press-fit fixation, depending on the preferred fixation method.

However, such reshaping has not been shown to provide a consistently suitable interface between the reshaped head and the femoral prosthesis. If the fit is not perfect, the Morse taper fit retention can be loosened. Further, a loose fit may result in micro- or macro-motion of portions of the prosthesis than are intended to be static, and may cause premature wear of the prosthesis. Moreover, the reshaping techniques for the femoral head have been adapted only for open surgery, and are not adapted for minimally or less invasive procedures to prepare the femoral head bone surface.

At the other interface of the hip prosthesis, the acetabular cup implant area must be prepared prior to positioning of the femoral head implant, in order to ensure a perfect fit thereof. Typically this involves removal of deteriorated or diseased bone surface at the acetabulum, but also carving the opening to match the size of an acetabular cup implant to be fitted. This is performed using an acetabular cup reamer. An acetabular cup reamer is typically a tool with a handle and a rotating head. As the acetabulum is reamed, the ground bone material is removed. Reamer heads of increasingly larger size (optionally provided as removable heads of one device) are used to enlarge the acetabulum to fit the socket implant.

An exact fit of the implant in the reamed acetabulum is critical as misalignment of the implant can lead to increased wear rate for the implant or improper seating of the implant leading to restricted leg movement and even hip dislocation.

The acetabulum is rich with blood vessels that supply blood to the hip joint. While the reamer is operated to prepare the acetabulum to receive the hip socket cup, the patient is subject to significant blood loss. Further, after the reamer is removed, exposing the prepared acetabulum, and while obtaining and implanting the hip socket cup thereat, the patient is subject to additional blood loss. Such blood loss can have significant consequences to the recovery of the patient.

Also, current methods for preparation of the acetabulum are also not well adapted or even suitable for less invasive hip replacement procedures.

SUMMARY

A prosthetic hip system generally includes acetabular components that are implanted in the pelvic bone, and femoral components that are implanted on the femoral head, as well as tooling for implanting the components.

The acetabular components generally include an acetabular socket, a polymer bushing received within the acetabular socket, and bone screws. In accord with one aspect of the system, the acetabular socket also defines an integrated reamer for preparing the acetabulum of the hip joint. More particularly, the acetabular socket has a generally hemispherical shape having interior and exterior surfaces, and a lip extending peripherally about an open end of the acetabular socket. The interior surface is preferably substantially smooth, whereas the exterior surface defines the structure of the reamer. The reamer includes one or more cutters, for example, in the form of teeth, that are adapted to break up bone in the acetabulum when the reamer is rotated or oscillated against the bone. The teeth may be provided in multiple rows and may be staggered in arrangement. The underside of the lip preferably also includes teeth or ridges adapted to seat the periphery of the socket against the bone. The axial center of the socket forms a K-wire hole for aligning the acetabular socket along the trajectory of an axis defined by a K-wire. The interior surface of the socket defines a central driver socket that is adapted to receive a manual or powered tool to rotate or oscillate the hip socket in a reaming action. One or more screw holes may be provided through the inner and outer surfaces of the acetabular socket, and removable threaded caps are inserted into the screw holes. The threaded caps may have conical tips that extend beyond the outer surface of the socket and aid in reaming action when the socket is rotated or oscillated. The threaded caps may be removed to receive cortical screws that extend within the screw holes of the acetabular socket and into the pelvic bone to further secure the acetabular components to the pelvic bone.

The bushing is made of a high-density polymer. The bushing includes inner and outer surfaces. The outer surface cooperates with the inner surface of the acetabular socket, and includes a plug that is received in the driver socket of the acetabular socket to rotationally lock the bushing relative to the acetabular socket. The inner surface is smooth, has a spherical curvature, and forms a bearing surface for a femoral head cover.

The femoral components generally include a cutter cap, a femoral head cover, and a coupling screw. The cutter cap includes a plurality of sides forming a polygonal periphery, an open end, and a closed end. In an embodiment, the sides form open and closed ends that are rectangular, and more preferably square in shape. The sides at the open end are sharp, defining cutters that under force are adapted to cut the bone along the sides of the femoral head to reshape the femoral head into a rotationally asymmetric shape. The closed end is adapted to couple to tooling to advance the cutter cap in a cutting action and onto the femoral head. The sides are preferably perforate to encourage bone ingrowth.

The femoral head cover replaces the function of the anatomical femoral head includes a spherical head having an outer surface adapted to articulably bear against the inner surface of the bushing, an inner polygonal opening sized and shaped to be stably received over implanted cutter cap, and a threaded screw hole axially positioned between the polygonal opening and the outer surface. In an embodiment, the polygonal opening is square in cross-sectional shape.

The coupling screw includes a large flat head, and a shaft threaded at its proximal and distal ends, and non-threaded along a central portion thereof. The proximal threads are cortical threads, and the distal threads are machine threads that are adapted to engage the threaded screw hole of the head cover. The coupling screw is adapted to be advanced from the lateral size of the femur and into engagement with the head cover to secure the head cover to the femoral head.

Various tools are also provided for use in implanting the acetabular and femoral components. One or more K-wires are used as alignment guides at one or both of the acetabulum and proximal femur. A driver shaft is provided for engaging the acetabular socket and has a distal end that plugs into the central driver socket to provide a rotational force to the socket. The driver shaft may be torqued under manual or motorized force. The driver shaft is adapted to provide sufficient force between the acetabular socket and the acetabulum to break up bone. A mallet is providing for seating the acetabular socket at the acetabulum after the bone is abraded. A cannulated drill is provided for drilling a hole over a K-wire and through the femoral head neck and femoral head. A first cutter is providable on a shaft and adapted to remove a portion of the femoral head to a flat. A second cutter is providable on the shaft. The second cutter includes the cutter cap and a nut that couples the cutter cap to the shaft, and is adapted to cut and remove the side portions of the femoral head below the flat.

The hip prosthesis system may be generally used as follows. The hip joint of the patient is surgically exposed, preferably through a small minimally (or less) invasive surgical opening, and the joint is dislocated. A flat is cut on the femoral head opposite the neck of the femur. Side portions of the femoral head below the flat are cut away to provide the femoral head with rotational asymmetry and preferably a polygonal cross-section. The femoral head cover is engaged over the reshaped femoral head. The acetabular socket is attached to a drive shaft and positioned in the acetabulum. The drive shaft is operated to cause the reamer on the exterior surface of the acetabular socket to abrade the bone tissue in the acetabulum. Preferably without removing the abraded bone tissue, the socket is then forced into intimate contact with the acetabular bone. The bushing is positioned within the acetabular socket, and the femoral head with femoral head cover is inserted into the bushing.

The system, tools, and method provide several advantages. At the acetabular side, by combining the socket and a reamer, the reamer does not need to be removed from the reamed acetabulum before positioning the socket. The reaming operation can open blood vessels; however, because the reamer is part of the socket and implanted at the acetabulum, the exposure of the reamed acetabulum and blood loss that would occur during the time for the removal of a reamer and subsequent implantation of a socket is eliminated. Also, the cortical and cancellous bone ground during reaming is preserved at the implantation site and contributes to bone ingrowth and new bone growth to secure and stabilize the socket, optionally without additional screws.

Further, at the femoral side, while the femoral head is reshaped, it is retained. This provides sufficient anatomical material in the event a later revision is required at the joint. Also, the rotational asymmetry formed at the femoral head and corresponding shaped recess in the femoral head cover provided rotational stability between the head cover and the femoral head. The system maintains such engagement and stability even if the femoral head and head cover are subject to longitudinal displacement away from each other.

The acetabular components may be used with the above-described femoral components or may be used with different femoral components having different features. The femoral components may also be used with different acetabular components having different features.

These and other features and advantages will be more clearly understood from the following detailed description taken in conjunction with the accompanying drawings and claims.

BRIEF DESCRIPTION OF THE DRAWINGS

FIG. 13 is a perspective view of a femoral head cutting bit used in implantation of the system.

FIG. 14 is a transparent side elevation of a slap hammer assembled with a cutter cap and cap nut.

FIG. 15 is a perspective view of the cap nut used to couple the cutter cap to a slap hammer in implantation of the system.

FIG. 16 is a plan view of the cap nut of FIG. 15.

DETAILED DESCRIPTION OF THE PREFERRED EMBODIMENTS

With reference to the following description, the terms "proximal" and "distal" are defined in reference to the hand of a surgeon or other medical professional implanting the hip system, with the term "proximal" being closer to the surgeon's hand, and the term "distal" being further from the surgeon's hand such as to often, but not necessarily, be located closer to the articular aspect of the hip joint.

The following system is intended for use in repair of a human joint. However, the system is not limited to repair of human joints, and can be adapted for implantation in animals including other mammals.

Prosthetic Hip System

Figure 1:
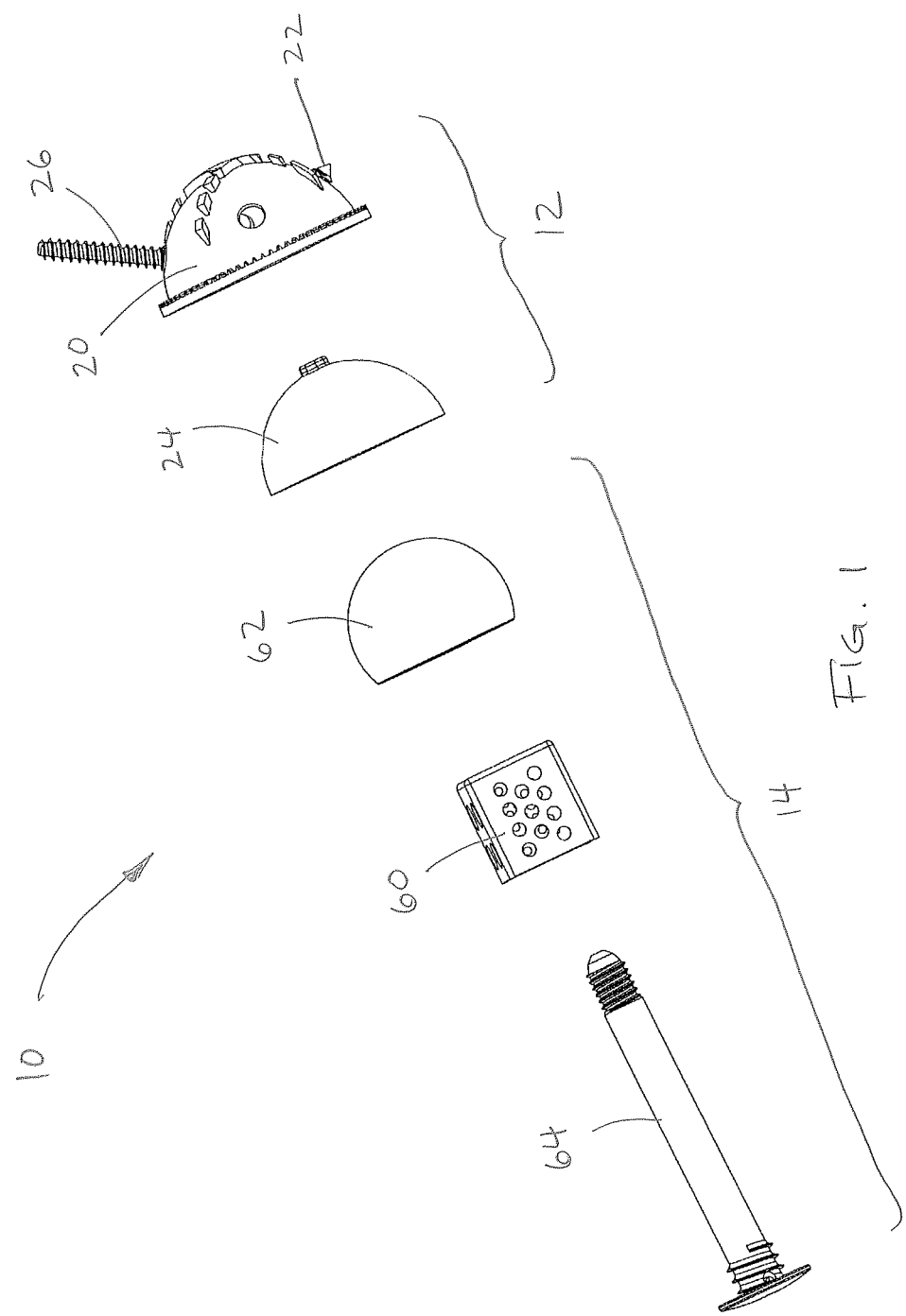
FIG. 1 is a partially exploded view of prosthetic hip system.

Referring to FIG. 1, a prosthetic hip system 10 according to an embodiment of the invention is shown. The system 10 generally includes acetabular components 12 that are implanted in the pelvic bone, and femoral components 14 that are implanted on the femoral head, as well as tooling for implanting the components, described below.

The acetabular components 12 generally include an acetabular socket 20, threaded caps 22 received within a wall of the socket, a bushing 24 received within the acetabular socket, and one or more bone screws 26. The acetabular socket 20, caps 22, and bone screws are all rigid structures, and preferably made from a biocompatible metal, including, but not limited to, stainless steel, titanium or titanium alloy, cobalt chromium, or other suitable implantable metals. The bushing is preferably made from a high-density, low friction biocompatible material, such as ultra high molecular weight polyethylene (UHMWPe) or another suitable polymer.

Figure 2:
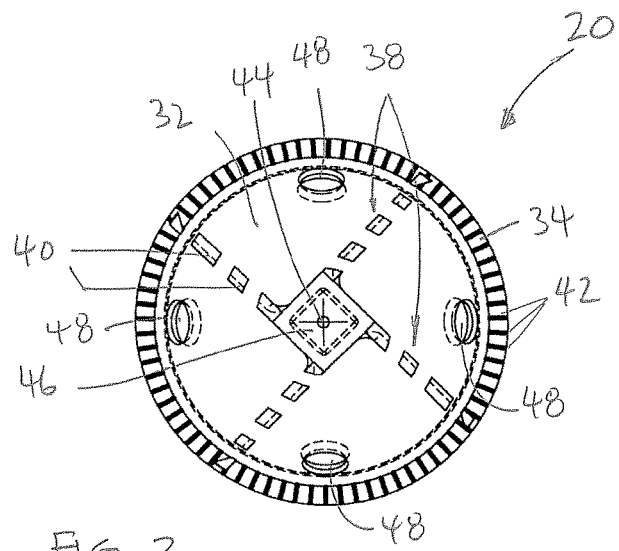
FIG. 2 is a top view of an acetabular socket of the system.
Figure 3:
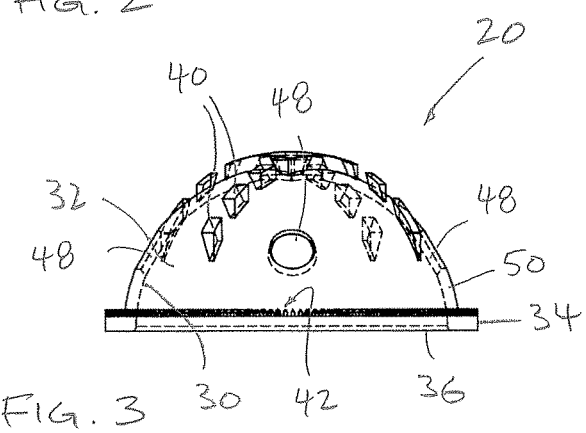
FIG. 3 is a side elevation view of the acetabular socket of the system.
Figure 5:
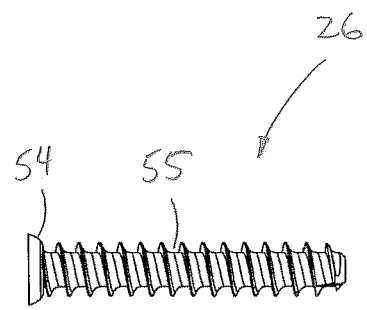
FIG. 5 is a side elevation view of a bone screw of the system.

More particularly, turning to FIGS. 2 and 3, the acetabular socket 20 is a hemispherical dome-shape shell having interior and exterior surfaces 30, 32, and a lip 34 or other 'guard' structure extending peripherally about an open end 36 of the acetabular socket. In accord with one aspect of the system, the acetabular socket 22 defines a reamer 38 on the exterior surface 32 for preparing the acetabulum of the hip joint to receive implantation of the socket. The reamer 38 includes one or more cutters 40, for example, in the form of teeth that are adapted to break up bone in the acetabulum when the reamer is rotated or oscillated against the bone. The cutters 40 may be provided in multiple rows and may be staggered in arrangement. The underside of the lip 34 preferably also includes teeth or ridges 42 adapted to stably seat the periphery of the socket against the bone. The axial center of the acetabular socket 20 forms a K-wire hole 44 for advancing the acetabular socket over a trajectory defined by a K-wire. The interior surface 30 is preferably substantially smooth, but defines a central driver socket 46 that is adapted to receive a manual or powered tool to apply a torque to rotate or oscillate the acetabular socket 20 in a reaming motion. The driver socket 46 is preferably polygonal in shape, more preferably rectangular, and even more preferably square in shape. One or more threaded screw holes 48 are provided through a wall 50 of the acetabular socket 20 between the inner and outer surfaces 30, 32 of the acetabular socket. The threaded caps 22 are removably inserted within the screw holes 48 (FIG. 1). The threaded caps 22 each have a head 51, a short section of machine threads 52, and a conical tip 53 that extend beyond the outer surface 32 of the acetabular socket when the cap 22 is threaded into the screw hole 48 in the wall 50 of the acetabular socket. The head 51 is low profile to seat substantially flush to the inner surface 30 of the acetabular socket. The extending conical tips 53 aid in reaming action when the acetabular socket 20 is moved in a reaming motion. The threaded caps 22 may be removed to open the threaded holes 48 to receive the cortical bone screws 26. The bone screws 26 (FIG. 5) each have a head 54 and a shaft 55 provided with cortical bone threads. The head 54 is adapted to seat substantially flush to the inner surface 30 of the acetabular socket 20 when the bone screw 26 extends within the threaded holes 48. The shaft 55 is adapted to enter into the pelvic bone to further secure the acetabular components to the pelvic bone. Four threaded holes 48 are shown, but none of the threaded caps 22 necessarily need be removed during surgery and the acetabular socket 20 is adapted to stably seat in the pelvic bone even without their use. However, the location of four threaded screw holes 48 provide various opportunities for one, two, three or even four bone screws 26 should the surgeon be of the opinion that a particular patient and procedure would benefit thereby. The threaded caps 22 provide a seal in the wall 50 between the interior and exterior surfaces 30, 32 in the absence of use of bone screws 26 within the respective screw holes 48. Fewer or more threaded screw holes 48 and threaded caps 22 may be provided to the socket 20.

Figure 6:
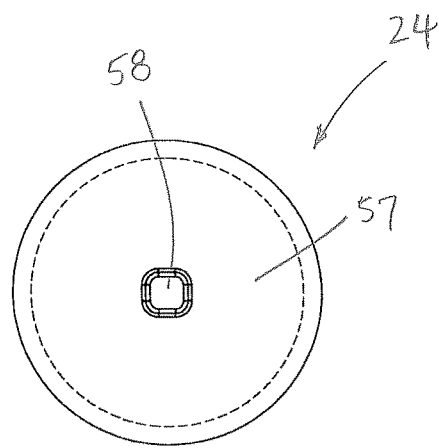
FIG. 6 is a top view of a bushing of the system.
Figure 7:
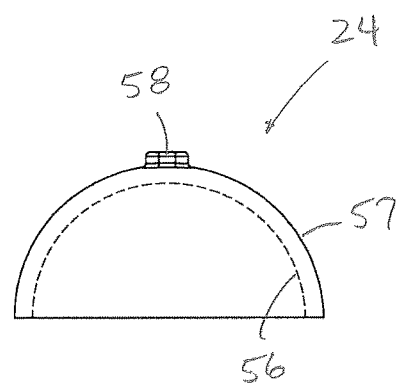
FIG. 7 is a top view of the bushing of the system.
Figure 4:
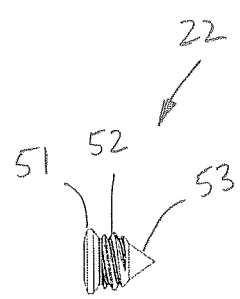
FIG. 4 is a side elevation view of a threaded cap of the system.

Referring to FIGS. 1, 6 and 7, the bushing 24 includes inner and outer surfaces 56, 57. The outer surface 57 of the bushing 24 cooperates with the inner surface 30 of the acetabular socket 20, and includes a plug 58 that is received in driver socket 46 (FIG. 2) of the acetabular socket to rotationally lock the bushing 24 relative to the acetabular socket 20. The inner surface 56 is smooth, has a spherical curvature, and forms a bearing surface for the femoral head cover 62, described below. The bushing 24 seats flush with the lip 34 at the open end 36 of the acetabular socket 20.

The femoral components 14 generally include a cutter cap 60, the femoral head cover 62, and a coupling screw 64. The femoral components are preferably made from metal, including, but not limited to, stainless steel, titanium or titanium alloy, cobalt chromium, or other suitable implantable metals.

Figure 8:
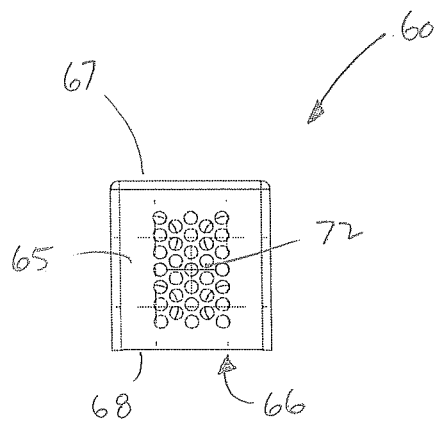
FIG. 8 is a side elevation view of a cutter cap of the system.
Figure 9:
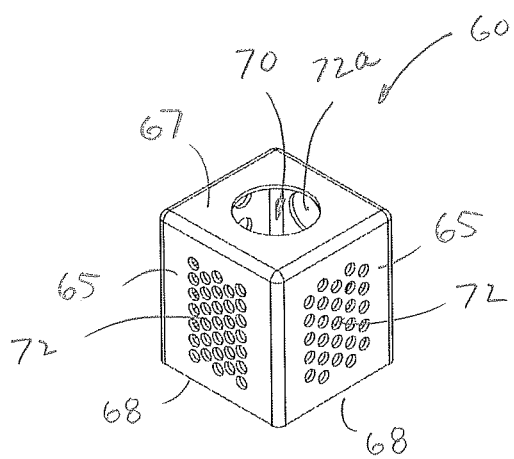
FIG. 9 is a perspective view of the cutter cap of the system.

Referring to FIGS. 8 and 9, the cutter cap 60 includes a plurality of sides 65 forming a polygonal periphery, an open end 66, and a partially closed end 67. In an embodiment, the sides 65 form open and partially closed ends that are rectangular, and more preferably square in shape. The sides 65 at the open end 66 are sharp, defining cutters 68 that under force are adapted to cut the bone along the sides of the femoral head into a rotationally asymmetric shape, such as a square shape. The partially closed end 67 includes a hole 70 adapting the cutter cap to receive tooling therethrough to advance the cutter cap in a cutting action onto the femoral head, as described below. The cutter cap 60 functions both as a cutter to cut the sides from the femoral head as well as form an implantable scaffold-like support that is implanted onto the femoral head, as described in more detail below. The sides 65 are preferably perforate (at 72) to encourage bone ingrowth in the subsequent implanted state. The sizes of the perforations may be the same about all the sides 65 or may be different; 72a illustrates a larger perforation than other illustrated perforations 72.

Figure 10:
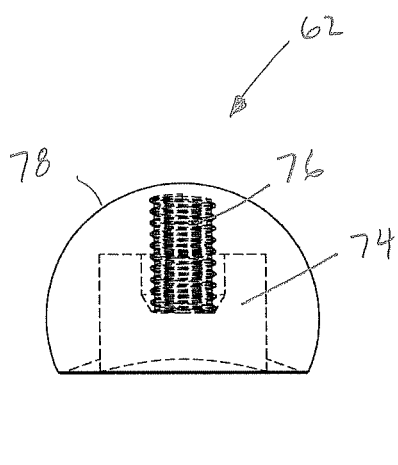
FIG. 10 is a transparent side elevation view of a femoral head cover of the system.
Figure 11:
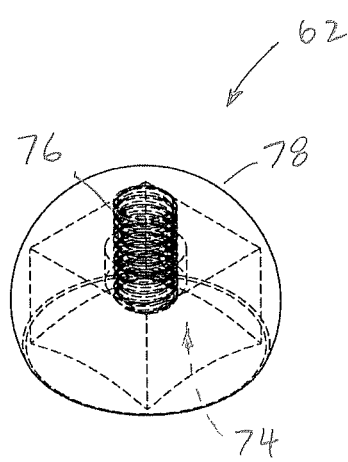
FIG. 11 is a transparent perspective view of the femoral head cover of the system.

Turning to FIGS. 10 and 11, the femoral head cover 62 replaces the function of the anatomical femoral head as a bearing surface. The head cover 62 includes a polygonal inner opening 74 sized and shaped to be stably received over implanted cutter cap 60, and a threaded screw hole 76 axially positioned between the polygonal opening 74 and an outer surface 78 of the head cover 62. In an embodiment, the polygonal opening is square in cross-sectional shape. The shape may be otherwise, provided that it rotationally locks with the cutter cap 60. The outer surface 78 of the head cover 62 is spherical and has a size adapted to articulably bear against the inner surface 54 of the bushing 24.

Figure 12:
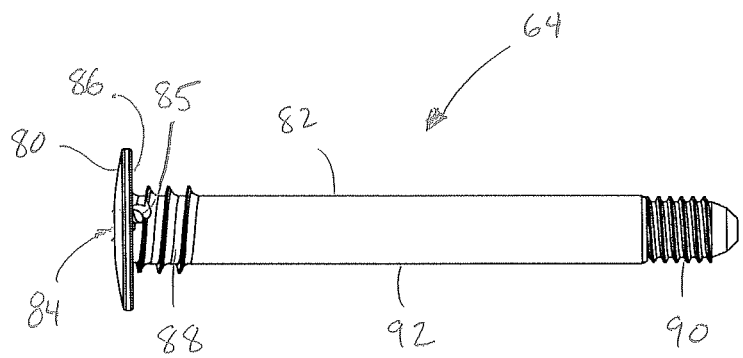
FIG. 12 is a side elevation of the flat head screw of the system.

As shown in FIG. 12, the coupling screw 64 includes a large head 80 and a shaft 82. The head 80 includes a driver recess 84 providing access to a screw hole 85 extending out of the shaft 82. The underside 86 of the head 80 (facing the shaft) is flat. The shaft 82 is threaded at its proximal end with bone engaging cortical threads 88, and threaded at its distal end with machine threads 90 adapted to engage the threaded screw hole 76 of the head cover 62, and preferably provided all therebetween (i.e., at a central portion 92) without threads. The cortical threads 88 have a major diameter greater than the diameter of the central portion 92, and a minor diameter equal to the diameter of the central portion. The machine threads 90 have a major diameter equal to the diameter of the central portion 92, and a minor diameter small than the diameter of the central portion. The coupling screw 64 is adapted to be advanced from the lateral size of the femur, over a K-wire and through a hole along the axis of the neck of the femoral head, and into engagement with the head cover to secure the head cover 62 to the anatomical femoral head, all as described hereinafter.

Prosthesis Implantation Tools

Various tooling is also provided for use in implanting the acetabular and femoral components. One or more K-wires are used as alignment guides at one or both of the acetabulum and proximal femur. A driver is provided having for engaging the acetabular socket and has a distal end that is insertable into the central driver socket to seat therein and provide a rotational force to the socket. The driver may be rotated or oscillated under manual or motorized force. If under manual force, the driver includes an appropriate handle for manual engagement. If under motorized force, driver is preferably configured as a bit that is receivable in a motorized bit driver. The driver is adapted to provide sufficient force between the acetabular socket and the acetabulum to break up bone. A mallet is providing for seating the acetabular socket at the acetabulum after the bone is abraded. A cannulated drill is provided for drilling a hole over a K-wire and through the femoral head neck and femoral head. Such above devices are well known in the art.

Turning now to FIG. 13, a first cutting tool 100 is also provided to remove an end of the femoral head opposite the femoral neck. The tool 100 is removably supported on a shaft 102. The shaft 102 has a first drive end 104 engageable by a rotational driver, and a second threaded end 106. The tool 100 includes a central threaded hole 107 that received the second threaded end 106. The threaded second end 106 and hole 107 have threads that extends counter to the rotational direction at which the first cutting tool 100 is intended to be rotated during cutting. In this manner, after threaded engagement, the tool 100 does not unintendedly loosen from the shaft 102 during use. Alternatively, the cutting tool 100 may be integrally formed with a non-removable shaft. The tool 100 includes cutting blades 108 supported on the second end 106 and facing toward the first end 104. In an embodiment, two cutting blades 108 are configured to cut when rotationally driven on the shaft. The cutting blades 108 extend radially outward between the shaft 102 and a circular blade support 110. A shroud 111 may be coupled to the blade support 110 to at least partially cover the femoral head as the cutter is rotated to limit the spread of the cut bone from the femoral head, and prevent unintended cutting of surrounding tissues.

Referring to FIGS. 14, 15 and 16, the cutter cap 60 can also be coupled to the second end 106 of the shaft 102 and retained with a cutter nut 130 to define a second cutting tool 112. The cutter nut 130 has a flat base 134 with a plurality of peripheral rails 136. The flat base 134 abuts the partially closed end 67 of the cutter cap 60, while the rails 136 extend about and in close engagement with the sides 65 of the cutter cap to prevent rotation of the cutter cap 60 relative to the cutter nut 130. The threads 106 on the shaft 102 extend through the hole 70 on the cutter cap to engage within a threaded hole 138 in the base 134. The cutter cap 60 is arranged on the shaft 102 to orient the blades portions 68 of the sides 65 toward the handle first end 104 of the shaft 12.

Implantation Procedure

Figure 17:
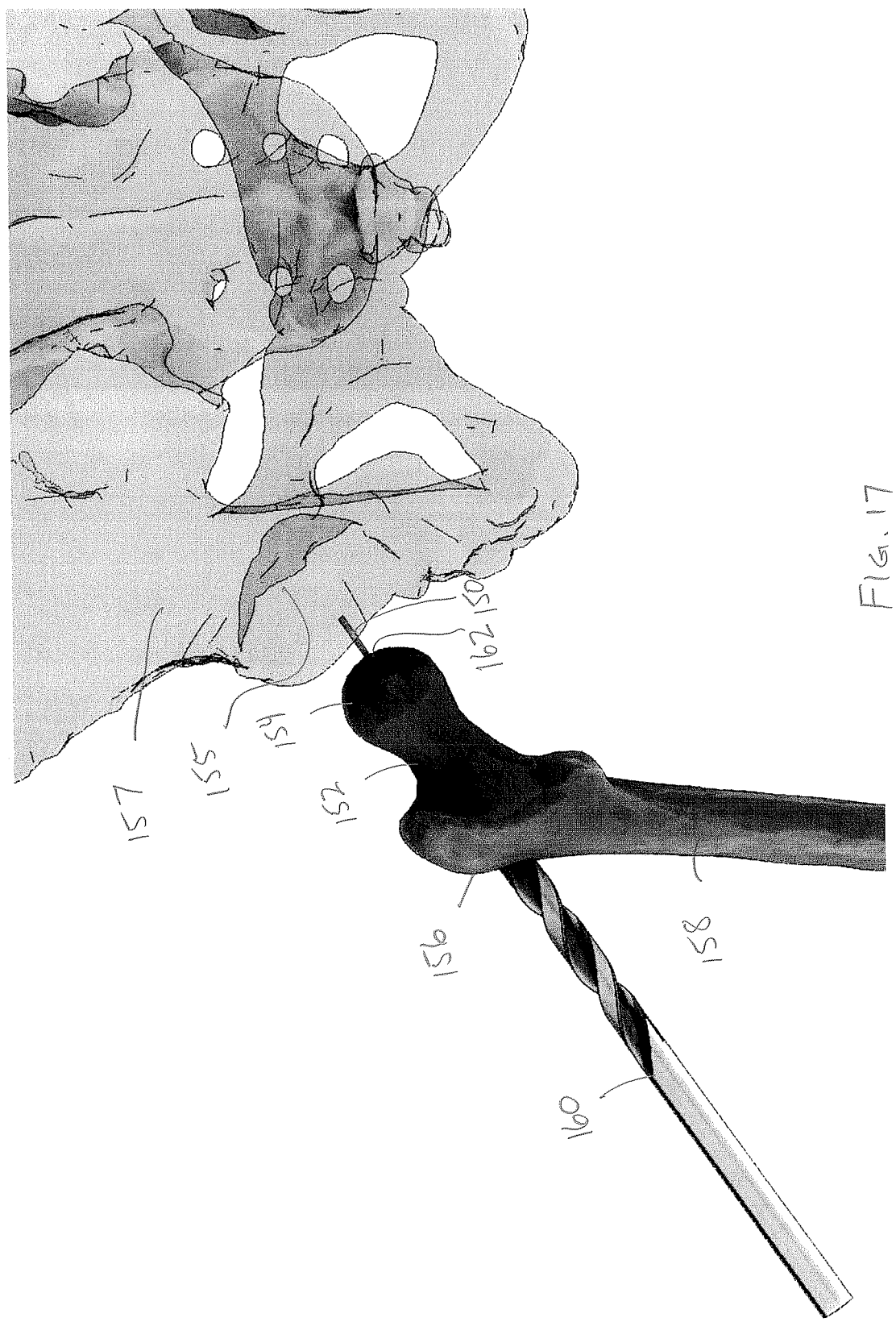
FIGS. 17 through 29 illustrate steps in a method for implanting the prosthetic hip system.

Referring now to FIGS. 17 through 29, the hip prosthesis system may be implanted in a patient as follows. The patient is arranged on a surgical table, preferably in a supine position, and prepped and draped. Referring to FIG. 17, the hip joint of the patient is accessed in a Smith-Petersen anterior approach, the joint is then exposed, and subsequently dislocated to separate the femoral head 154 from the acetabulum 155 of the pelvic bone 157. A K-wire 150 is advanced into the femoral neck 152 and femoral head 154 from the lateral side 156 of the femur 158. A cannulated drill 160 is then advanced and over the K-wire 150 to cut a hole 162 along the trajectory of the K-wire 150, and both the K-wire 150 and drill 160 are removed from the femur 158.

Figure 18:
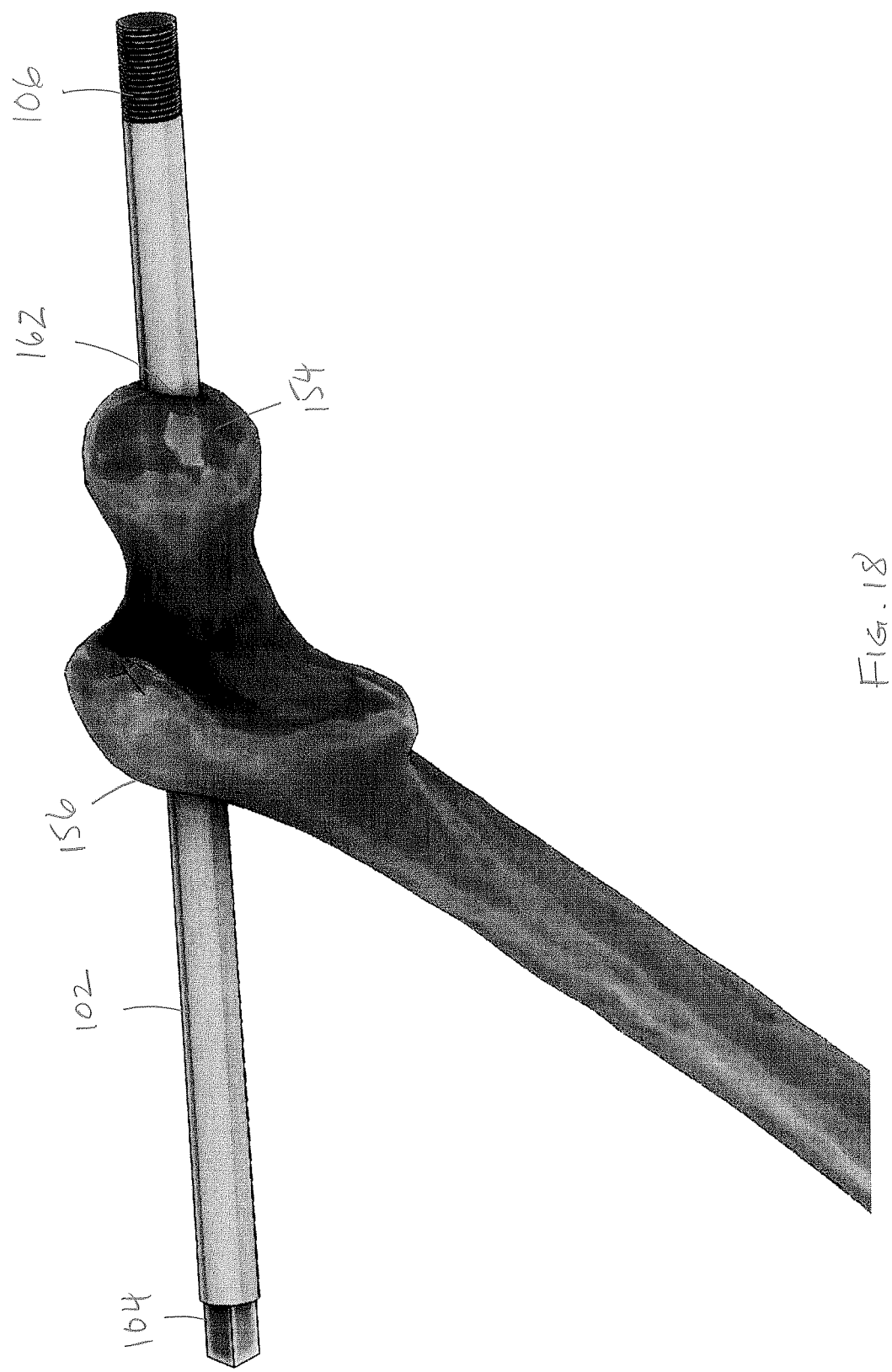
Figure 19:
Figure 20:
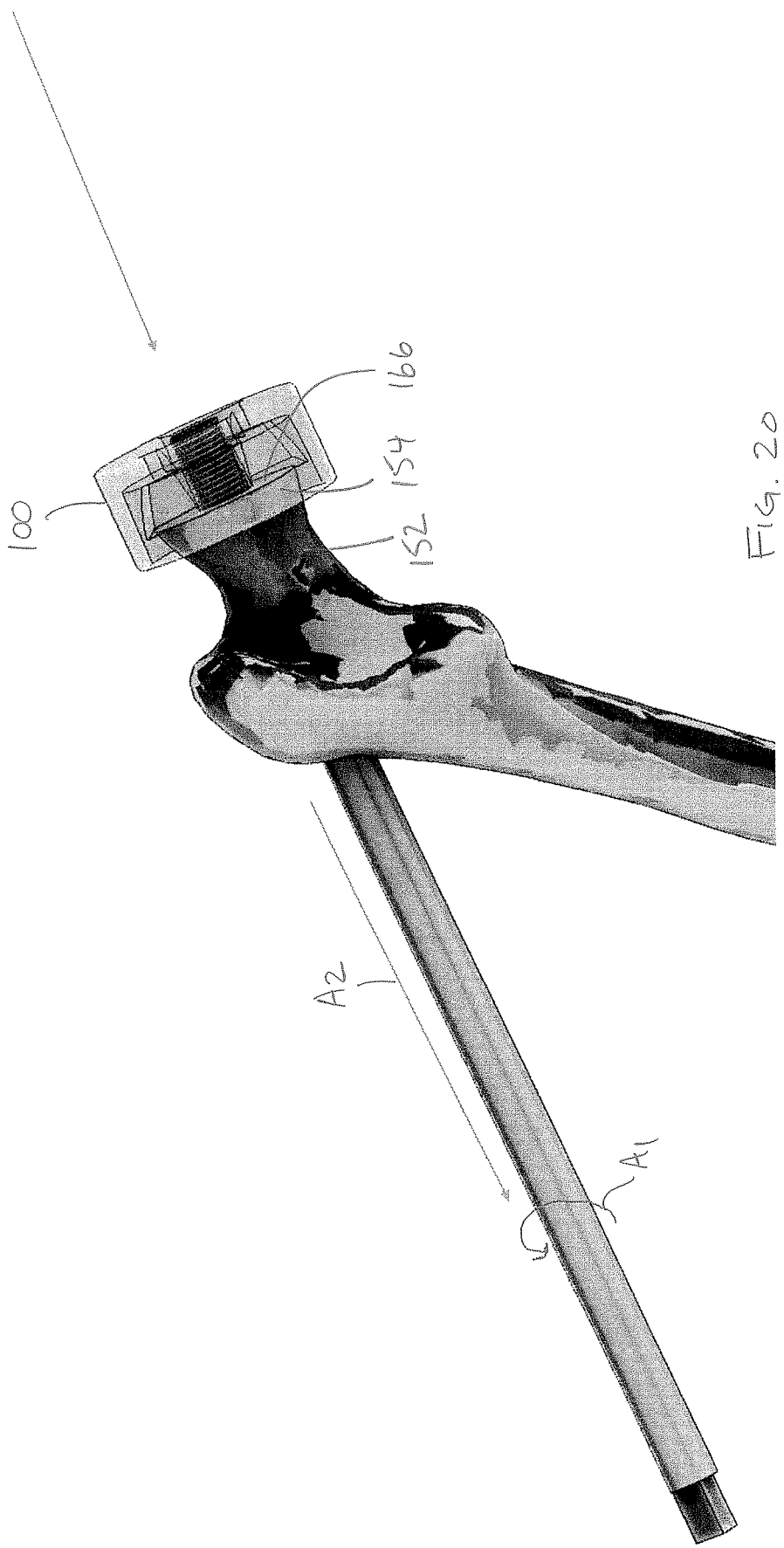

Turning to FIG. 18, the drive shaft 102 is inserted into the hole 162 from the lateral side 164. The threaded end 106 of the shaft 102 extends beyond the femoral head 154, while the drive end 104 extends from the lateral side 156 of the femur. Then, referring to FIG. 18, the first cutter 100 is attached to the threaded end 106 of the drive shaft 102. As shown in FIG. 20, the drive shaft 102 and consequently the first cutter 100 are rotated (as shown by arrow A1) and drawn laterally from the femoral head 154 toward the femoral neck 152 (in the direction of arrow A2) to cut a flat 166 on the femoral head 154 opposite the neck 152 of the femur. The shaft 102 is then decoupled from the first cutter 100, and the first cutter is removed.

Figure 21:
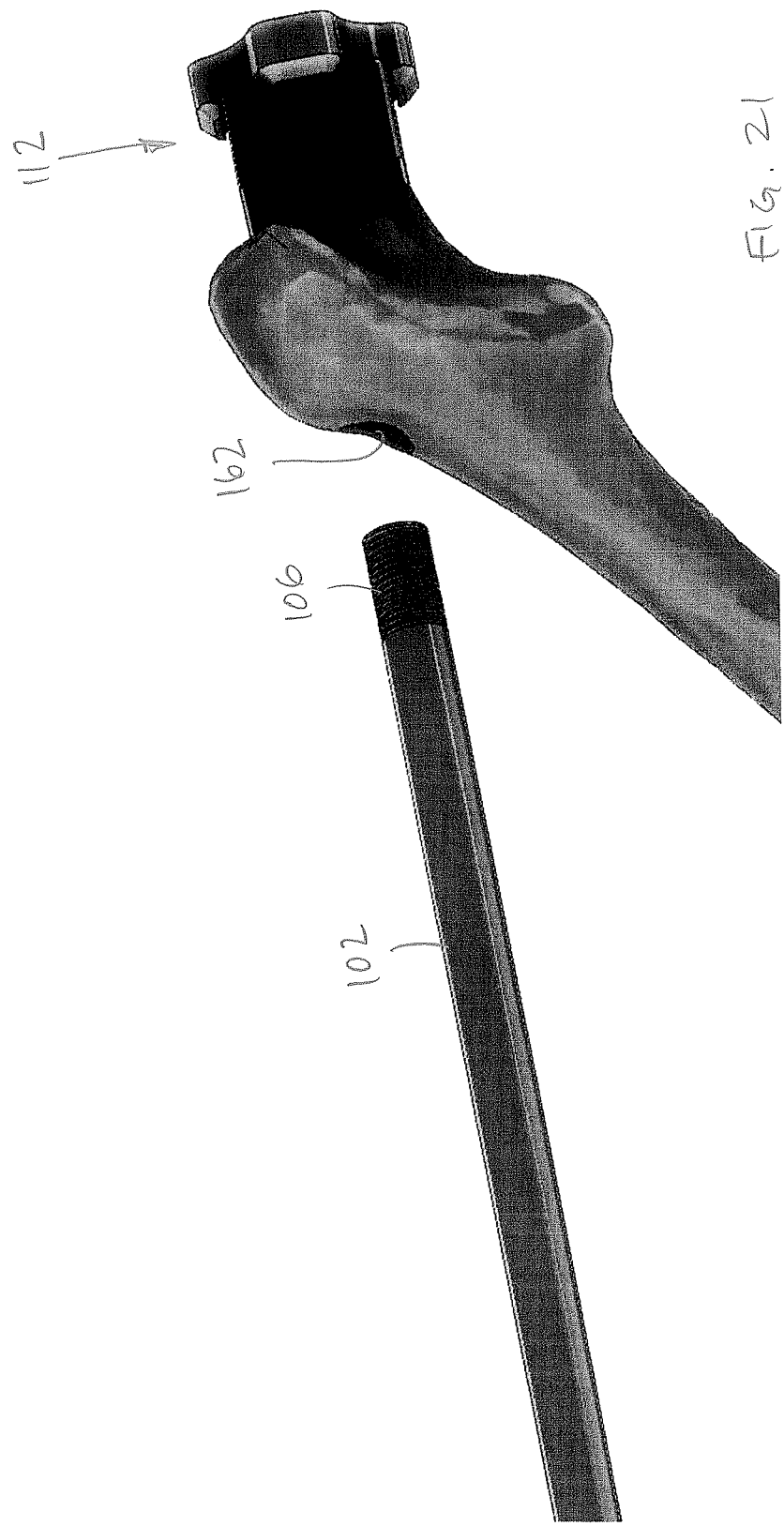
Figure 22:
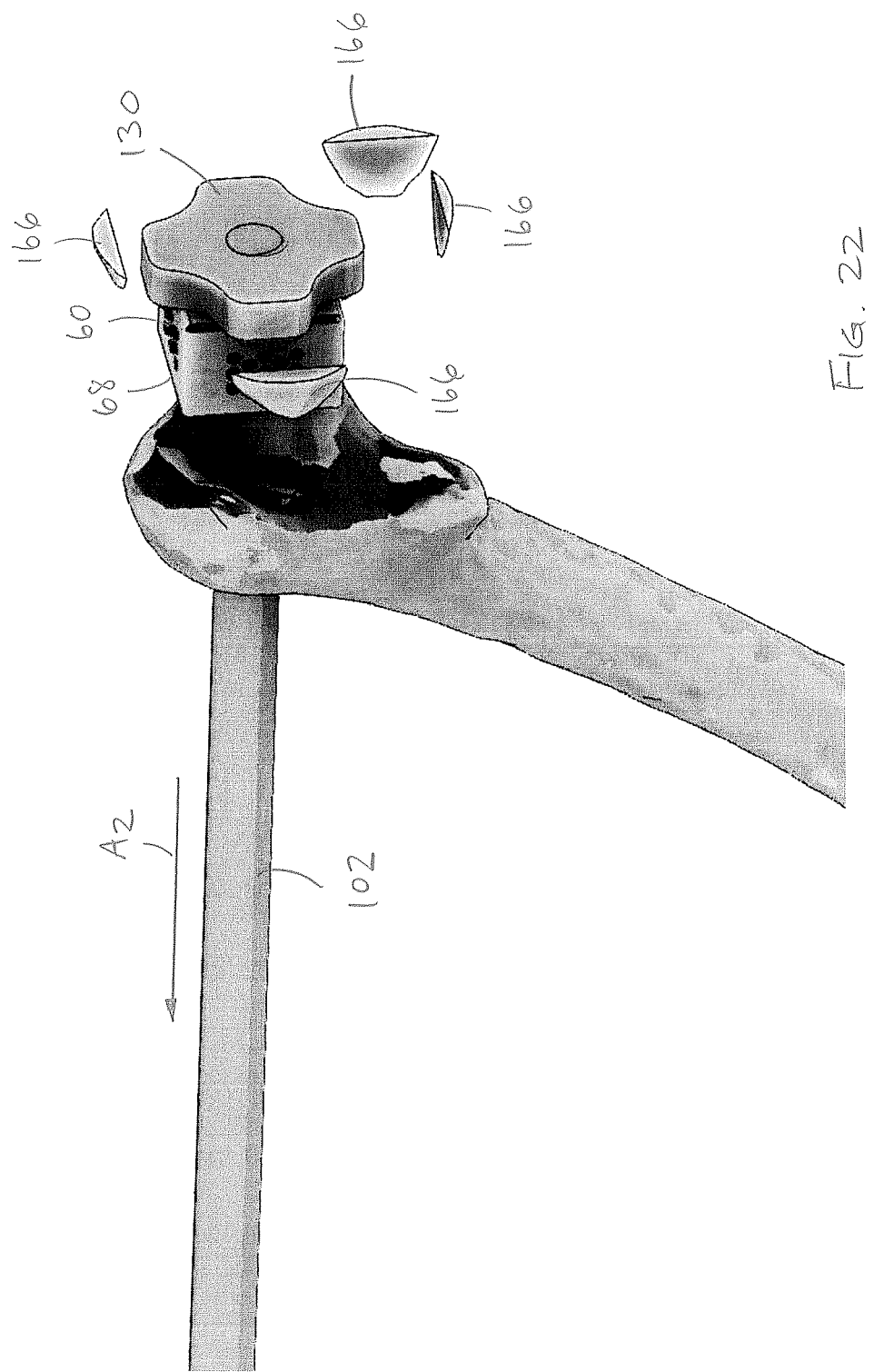
Figure 23:
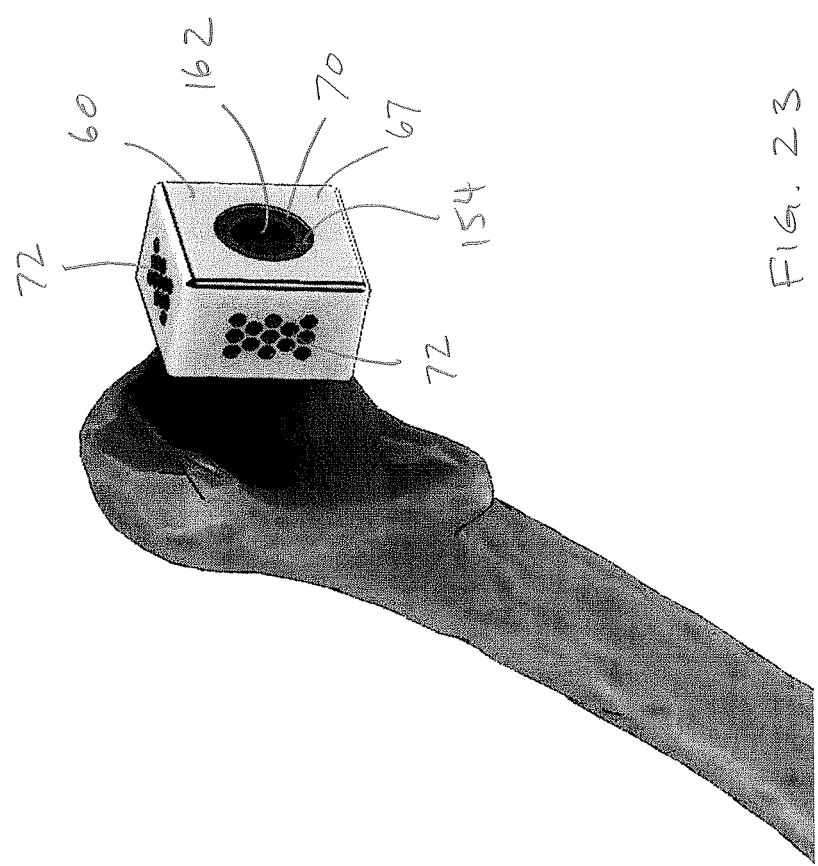

The second cutter 112 is then position at the femoral head, and the threaded end 106 of the shaft (if removed from the hole 162, is reinserted and) is threadedly engaged to the second cutter (FIG. 21). Then, as shown in FIG. 22, the shaft 102 is displaced in the direction of arrow A2 to force the blade portions 68 of the cutter cap 60 onto the flattened femoral head 154 (FIG. 20) to cut away the rounded side portions 166 of the femoral head. This provides the femoral head 154 with a rotationally asymmetric, non-circular cross-section having the same maximum size and shape as the cutter cap 60. Thus, when the cutter cap 60 is square in cross-section, the femoral head is provided with a square cross-sectional shape. As the cutter cap 60 is moved to remove the side portions from the femoral head, it is also advanced into implanted engagement over the re-shaped femoral head 154. The shaft 102 is then threadedly decoupled from the nut 130 (FIG. 22), the nut is removed from the surgical site, and the shaft is removed from the hole 162. As mentioned above, the cutter cap 60 adds structural integrity to the cut femoral head 154 and the perforations 72 aid in bone ingrowth for long-term stability (FIG. 23). The hole 70 in the partially closed end 67 of the cutter cap 60 aligns over the drilled hole 162 in the femur.

Figure 24:
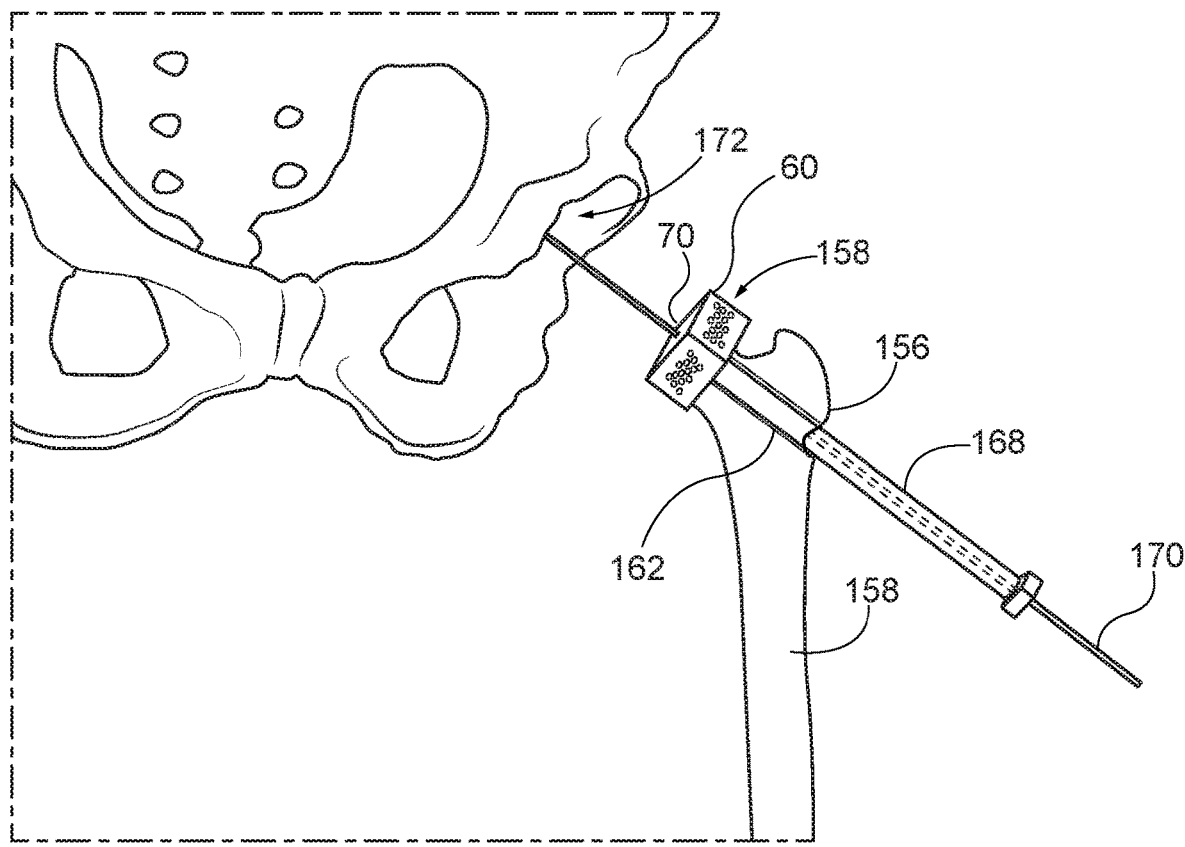

Turning now to FIG. 24, a K-wire guide 168 and K-wire 170 are then inserted through the hole 162 in the femur 158, from the lateral side 156 toward the head 154, out of the hole 70 in the cutter cap 60, and into the acetabulum 172. The K-wire 170 establishes an axial trajectory between the femoral head 154 and the acetabulum 172. The K-wire 170 is then withdrawn from the acetabulum 172. The acetabular socket 20 is then positioned at the acetabulum and the K-wire 170 is inserted through the K-wire hole 44 the acetabular socket 20 (FIG. 2). A socket driver shaft 174 is then advanced over the K-wire 170 and through the hole 162 in the femur until its driver end engages in the driver socket 46 of the acetabular socket 20 (FIG. 2). This allows the socket driver shaft 174 to apply a torque to the acetabular socket 20 when the socket driver shaft is torqued. The socket driver shaft 174 is then rotated (or oscillated) manually or with a motorized tool (not shown) to drive the reamers 38 of the acetabular socket 20 against the cortical and cancellous bone of the acetabulum 172 to break up the bone to provide an appropriate fit for the acetabular socket 20 on the pelvic bone 176. A slurry of cortical and cancellous bone material is generated between the acetabular socket 20 and the acetabulum 172. Then, once the acetabulum 172 is sufficiently reamed, preferably without removing the bone slurry or the acetabular socket 20 from the acetabulum, (1) the socket driver 174 and K-wire 170 are removed from the acetabular socket 20, and (2) the acetabular socket 20 is implanted in the acetabulum 172. Several advantages are provided. Because the slurry from the reaming of cortical and cancellous pelvic bone is maintained at the implantation site, the method takes advantage of osteogenesis that is fostered by the bone slurry. Further, blood loss is limited. In current procedures, during the time between removing a reamer and implanting a separate socket, there is significant blood loss from the exposed reamed bone. The present procedure is significantly quicker and does not expose the bone in a manner that allows it to bleed.

Figure 26:
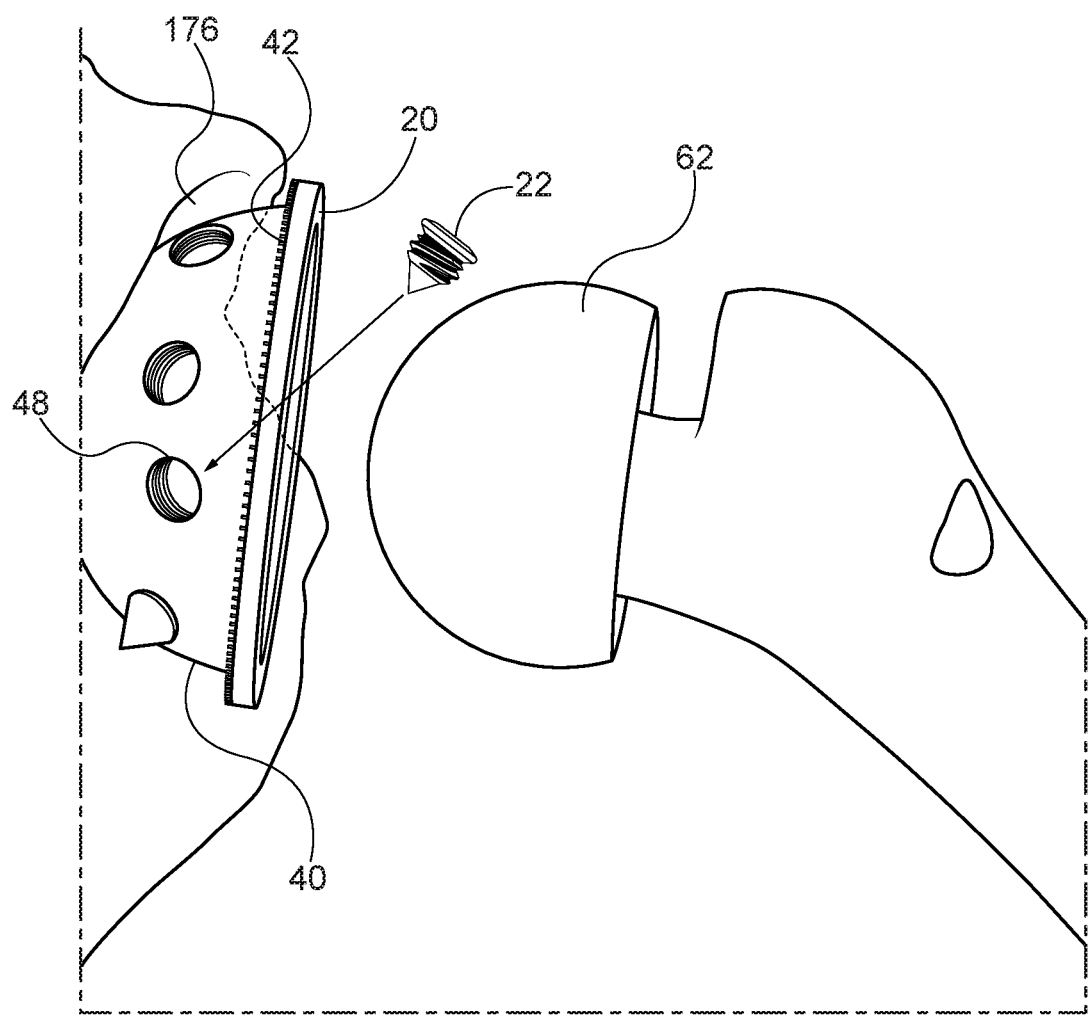

Referring to FIG. 26, the acetabular socket 20 is secured at the acetabulum 172 by tapping the acetabular socket down with the mallet (not shown). The mallet is used to cause the reamer teeth 40 and the lip teeth 42 to engage the pelvic bone 176 to stabilize the acetabular socket 20. If additional stabilization of the acetabular socket 20 is required, one or more of the threaded caps 22 are removed from the holes 48 in the acetabular socket 20, and the bone screws 26 (FIGS. 1 and 5) are inserted therethrough into the pelvic bone 176, e.g., to provide superior anchoring in the body of the ilium, to further secure the acetabular socket in at the acetabulum 172. Additionally, the peripheral lip 34 provides a guard against debris material from entering between the exterior surface 32 of the socket 20 and the acetabulum and causing erosion and a foreign body reaction that can lead to loosening of the implant. Suitable 'guard' structure other than lip 34 can alternatively be used.

Figure 25:
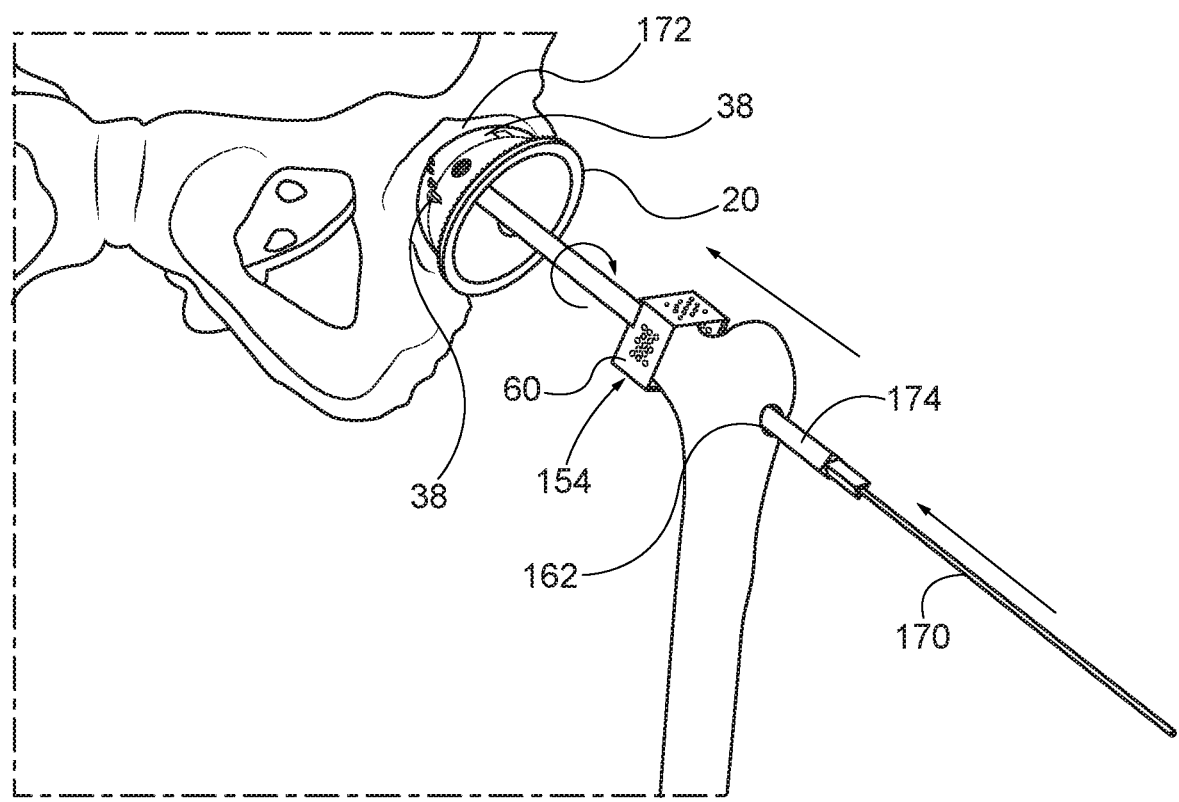
Figure 27:
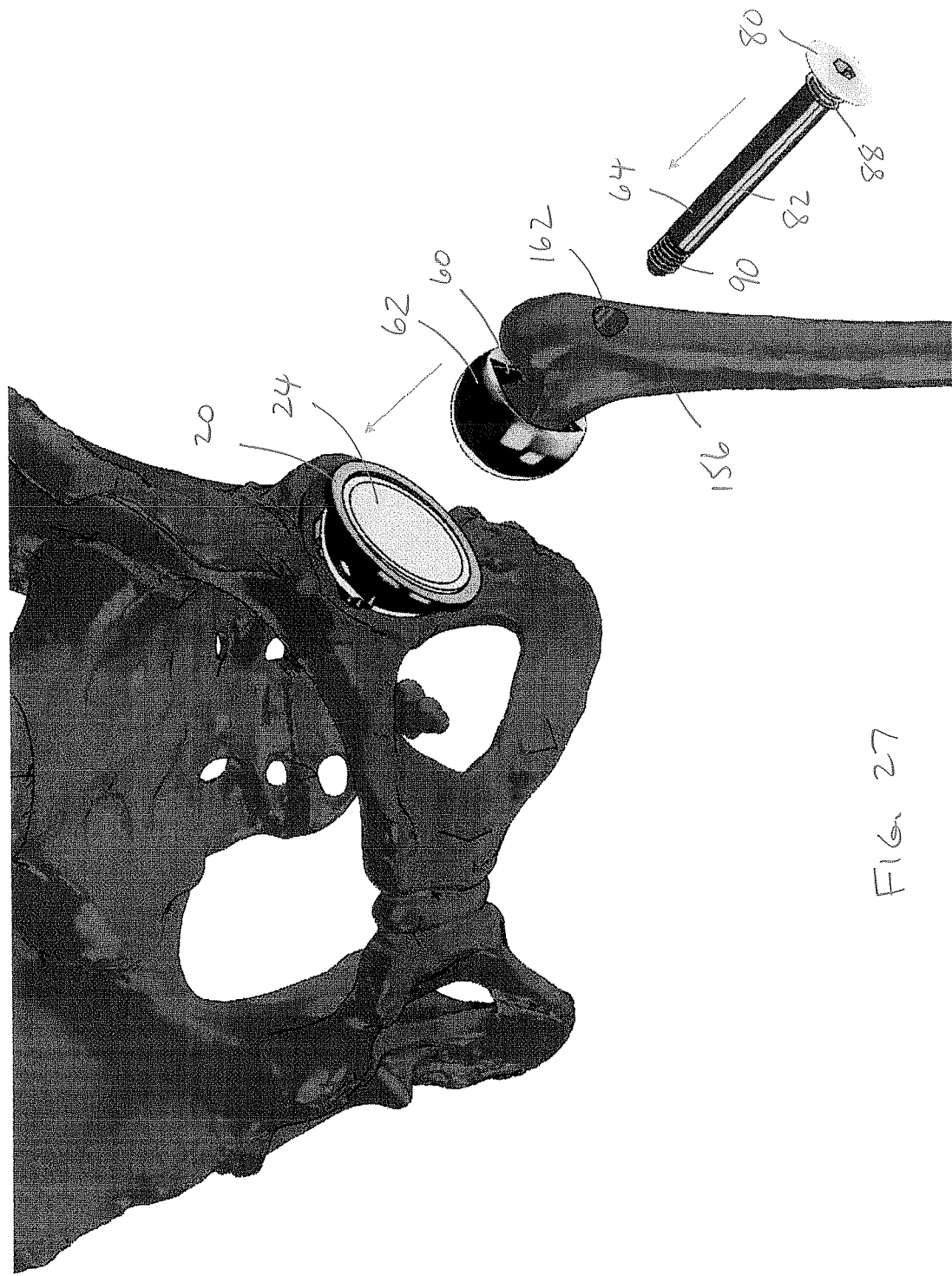

Still referring to FIG. 26, the femoral head cover 62 is positioned over the reshaped femoral head 154 and cutter cap 60 (shown in FIG. 25). Turning to FIG. 27, the bushing 24 is provided into the acetabular socket 20 (or onto the femoral head cover 62). Then the acetabular socket 20, bushing 24, and femoral head cover 62 are assembled together to check the mobility of the joint. If any longitudinal revision is required to the fit of the joint, the joint can be disassembled and adjusted. Such adjustment can be effected by removing additional bone material from femoral head (e.g., under the cutter cap) or by adding one or more washers (not shown) between the cutter cap 60 and the femoral head cover 62 (i.e., within the inner opening 74 of the femoral head cover).

Figure 28:
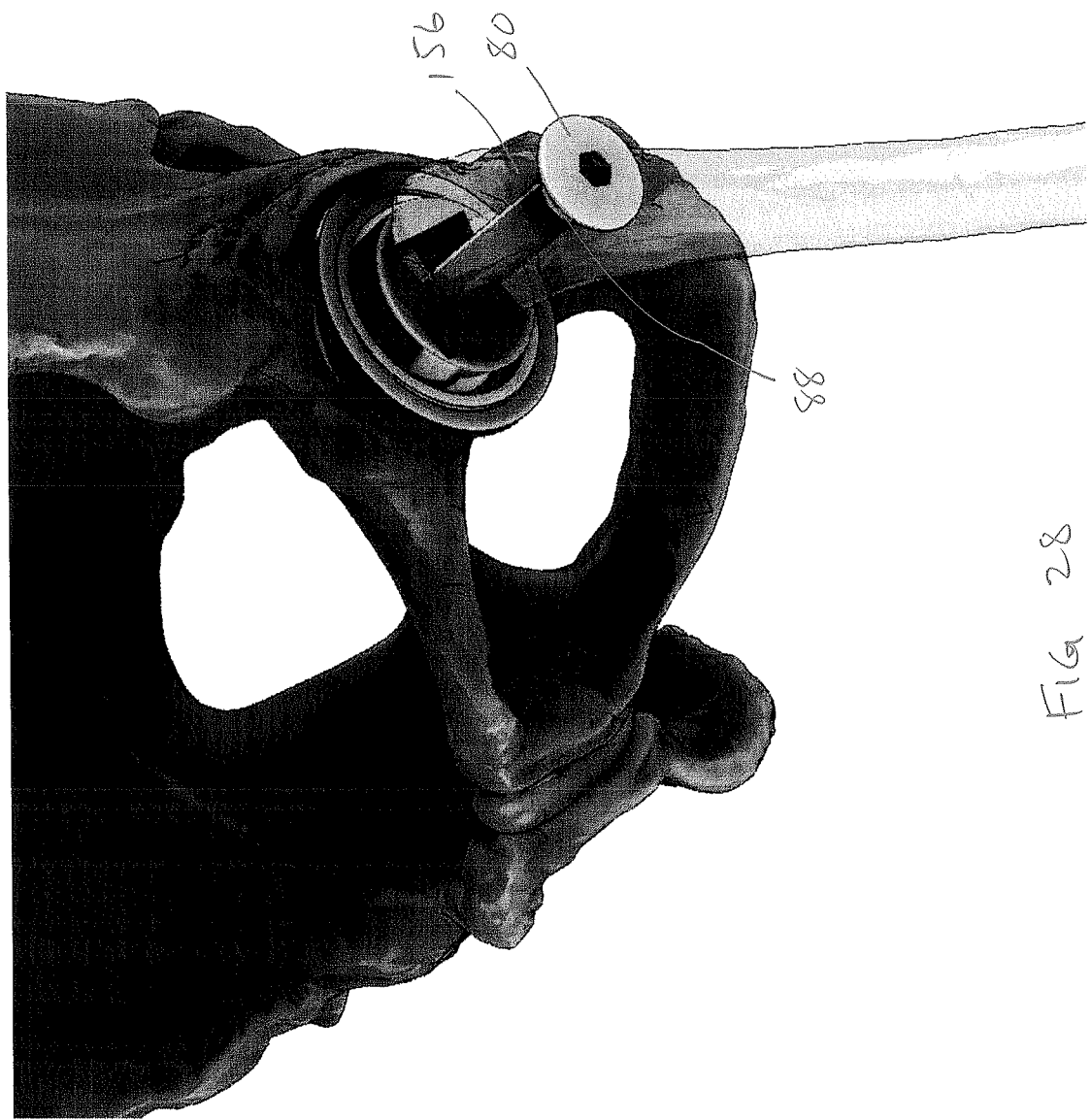
Figure 29:
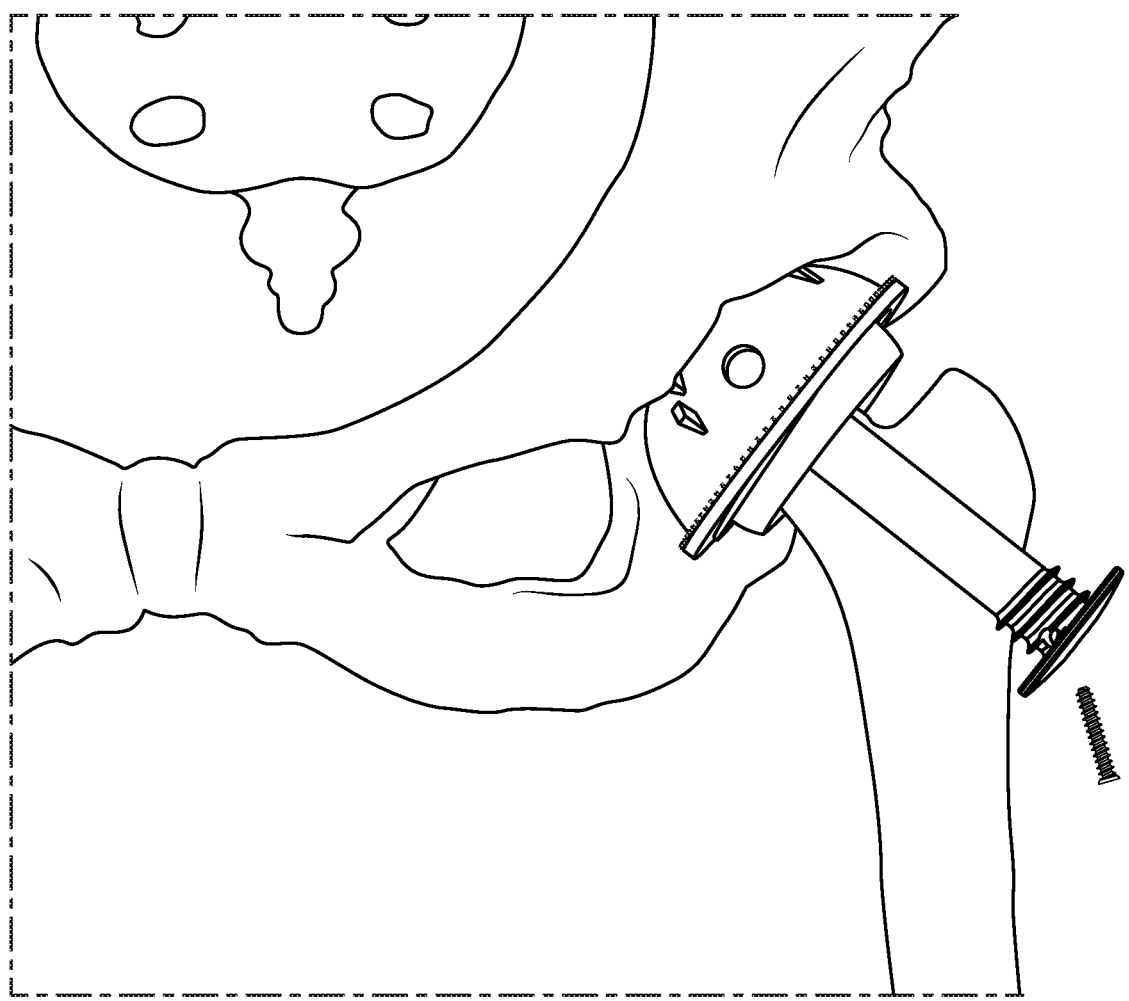

Referring to FIGS. 27 and 28, with the fit confirmed, the coupling screw 64 is then advanced through the drilled hole 162 in the femur and advanced until the machine threads 90 at the distal end of the shaft 82 engage into the threaded screw hole 76 of the femoral head cover 62 (FIGS. 10 and 11) and the cortical threads 88 at the proximal end of the shaft are secured in the drilled hole 162 and the head 80 resides in close contact with the lateral side of the bone. A screw 180 is then inserted through the screw hole 85 at the head 80 of the in the coupling screw 64 and into the bone to lock rotation of the coupling screw. The surgical incision is then closed using standard techniques.

The systems, tools, and methods described provide several advantages. As discussed above, at the acetabular side, by combining the socket and a reamer, the reamer does not need to be removed from the reamed acetabulum before positioning the socket. The reaming operation can open blood vessels; however, because the reamer is part of the socket and implanted at the acetabulum, the exposure of the reamed acetabulum and blood loss that would occur during the time for the removal of a reamer and subsequent implantation of a socket is eliminated. Also, the cortical and cancellous bone ground during reaming is preserved at the implantation site and contributes to bone ingrowth and new bone growth to secure and stabilize the socket, optionally without additional screws.

Further, at the femoral side, while the femoral head is reshaped, it is retained. This provides sufficient anatomical material in the event a later revision is required at the joint.

Also, the rotational interference from the rotational asymmetry formed at the femoral head and corresponding shaped recess in the femoral head cover provided rotational stability between the head cover and the femoral head. Many prior art system rely solely on a Morse taper, which maintains coupling via longitudinal interference, for the engagement between related components. However, unlike such systems, the described system maintains rotational engagement even if the femoral head and head cover are subject to longitudinal displacement away from each other. Also, unlike a system coupled solely via a Morse taper, the current system can be adjusted longitudinally, e.g., using one or more washers, without losing its rotational lock between components.

The systems and methods allow for a relatively minimally invasive procedure in which the tools to implant the system are operated along an axis extending through the neck and head of the femur from the lateral side of the femur and, thus, outside the patient. The operating space required to carry out the procedure is relatively confined and limited, permitting a smaller incision, less disturbance of tissue, less blood loss, and quicker post-operative healing. Further, the joint repair procedure can be quicker than prior procedures attempting reconstruction of the same joint and bone surfaces, as the procedure requires less tissue disruption during implantation, and less tissue repair after the system has been implanted at the joint.

The acetabular components may be used with the above-described femoral components or may be used with different femoral components having different features. The femoral components may also be used with different acetabular components having different features. Thus, either of the acetabular components or the femoral components can be used independently of the others.

There have been described and illustrated herein embodiments of a hip prosthesis system, tool for the implanting the system, and methods of implanting the system. While particular embodiments of the invention have been described, it is not intended that the invention be limited thereto, as it is intended that the invention be as broad in scope as the art will allow and that the specification be read likewise. Thus, while the cutter cap is disclosed as being implanted on the femoral head after reshaping the femoral head, it is recognized that after such reshaping the cutter cap can be removed and the reshaped femoral head can be inserted directly into the femoral head cover; albeit without the advantages that the implanted cutter cap provides, such as a supporting scaffold for the femoral head. Also, while particular materials have been disclosed, it will be appreciated that other materials can be used as well. It will therefore be appreciated by those skilled in the art that yet other modifications could be made to the provided invention without deviating from its scope as claimed.

What is claimed is:

1. A permanently implantable hip prosthesis system for replacement of a hip joint at the interface of a femoral head of a femur and an acetabulum of a pelvic bone, the system comprising:
    a) a permanent acetabular implant, including,
        i) a rigid dome-shaped shell defining an open end, an interior surface and an exterior surface,
        ii) at least one reamer on the exterior surface, the reamer adapted to break up bone in the acetabulum when the reamer is rotated or oscillated against the bone, and
        iii) a driver socket defined at the interior surface for applying a torque to rotate or oscillate the shell, the interior surface smooth surrounding the driver socket;
    b) a femoral head cover having an outer surface and adapted to be received over the femoral head;
    c) a bushing adapted to be positioned between the interior surface of the shell and the outer surface of the femoral head cover, the bushing having an outer surface that includes a rotationally asymmetric plug that rotationally interferes with the driver socket in the acetabular implant.

2. The system of claim 1, wherein:
the acetabular implant and femoral head cover are made from metal, and the bushing is made from a polymer.

3. The system of claim 1, further comprising:
a cutter cap having a plurality of sides forming a polygonal periphery, an open end, and a partially closed end, the sides at the open end being sharp to define bone cutters that under force are adapted to cut the femoral head of the femur along the sides of the femoral head into a rotationally asymmetric shape, and the partially closed end including a hole adapting the cutter cap to receive a shaft therethrough, the femoral head cover further including an inner opening sized and shaped to be stably received over the cutter cap in a rotationally fixed engagement, and a threaded screw hole axially positioned between the inner opening and the outer surface, and the cutter cap being positionable within the inner opening in a rotationally fixed engagement, with the hole in the cutter cap aligning with the threaded screw hole of the femoral head cover.

4. The system of claim 1, wherein:
the reamer of the acetabular implant comprises a plurality of cutting teeth.

5. The system of claim 1, wherein:
the bushing has a central axis, and a closed end through which the central axis extends.

6. The system of claim 1, wherein:
the bushing defines a continuous smooth inner bearing surface.

7. A method for implanting a prosthetic hip implant, comprising:
   a) accessing a hip joint comprising an acetabulum of a pelvis and a femoral head of a femur, the femur further having a femoral neck and a lateral side opposite the femoral head;
   b) first reshaping the femoral head opposite the neck of the femur to form a flat on the femoral head;
   c) second reshaping the femoral head between the flat and the femoral neck to remove peripheral portions of the femoral head and provide a reshaped femoral head with rotational asymmetry;
   d) then applying a femoral head cover over the reshaped femoral head, the femoral head cover having a non-circular recess that rotationally interferes with the reshaped femoral head; and
   e) inserting the femoral head cover into an acetabular socket in the acetabulum.

8. The method according to claim 7, wherein:
the first reshaping includes
   extending a driver shaft through a hole drilled in the femur, the hole extending from the lateral side through the femoral head,
   attaching a rotational first cutter to the driver shaft, and
   rotating the driver shaft from the lateral side of the femur and drawing the rotational cutter against the femoral head to form the flat.

9. The method according to claim 7, wherein:
the second reshaping includes
   attaching a second cutter to the driver shaft, and
   longitudinally forcing the second cutter against the flat.

10. The method according to claim 9, wherein:
the second cutter is implanted onto the reshaped femoral head and the femoral head cover is applied over the second cutter.

11. The method according to claim 7, wherein:
the second reshaping includes,
   extending a driver shaft through a hole drilled in the femur, the hole extending from
   the lateral side through the femoral head,
   attaching a cutter to the driver shaft, and
   longitudinally forcing the cutter against the flat.

12. The method according to claim 11, wherein:
the cutter is implanted onto the reshaped femoral head and the femoral head cover is applied over the cutter.

13. The method according to claim 7, further comprising:
inserting a bushing between the femoral head cover and the acetabular socket.

14. The method according to claim 7, further comprising:
attaching an implantable acetabular socket to a drive shaft, the acetabular socket having an interior surface and a bone contacting exterior surface, the exterior surface having bone-reaming structure;
positioning the exterior surface of the acetabular socket in the acetabulum;
reaming the bone by applying a rotational force the drive shaft to cause the bone-reaming structure to rotate or oscillate at the acetabulum; and
implanting the acetabular socket in the acetabulum to provide the acetabular socket in the acetabulum.

15. The method according to claim 14, wherein:
the acetabular socket is not removed from the acetabulum between reaming the bone and implanting the acetabular socket in the acetabulum.

16. The method according to claim 14, wherein:
reaming the bone generates a bone slurry, and the bone slurry is maintained between acetabular socket and the acetabulum.

17. A method for implanting a prosthetic hip implant, comprising:
   a) accessing, through a wound, a hip joint comprising an acetabulum of a pelvis and a femoral head of a femur, the femur further having a femoral neck and a lateral side opposite the femoral head;
   b) attaching an implantable acetabular socket to a drive shaft, the acetabular socket having an interior surface and a bone contacting exterior surface, the exterior surface having bone-reaming structure;
   c) positioning the exterior surface of the acetabular socket in the acetabulum;
   d) reaming the bone by applying a rotational force the drive shaft to cause the bone-reaming structure to rotate or oscillate at the acetabulum; and
   e) permanently implanting the acetabular socket in the acetabulum to provide the acetabular socket in the acetabulum;
   f) closing the wound with the acetabular socket in the acetabulum.

18. The method according to claim 17, wherein:
the acetabular socket is not removed from the acetabulum between reaming the bone and implanting the acetabular socket in the acetabulum.

19. The method according to claim 17, wherein:
reaming the bone generates a bone slurry, and the bone slurry is maintained between acetabular socket and the acetabulum.

20. An acetabular implant for a prosthetic hip system for repair of a hip joint having an acetabulum, including:
   a) a rigid dome-shaped shell defining an open end, an interior surface and an exterior surface;
   b) a reamer on the exterior surface, the reamer adapted to break up bone in the acetabulum when the reamer is rotated or oscillated against the bone;
   c) a driver socket defined at the interior surface for applying a torque to rotate or oscillate the shell, the interior surface smooth surrounding the driver socket;
   d) a K-wire hole defined at the center of the driver socket to allow the shell to be advanced along a trajectory defined by a K-wire; and
   e) a bushing having a smooth, low friction interior surface with a spherical curvature and an exterior surface, the bushing seated within the shell such that the exterior surface of the shell contacts the interior surface of the shell, the exterior surface of the bushing includes a rotationally asymmetric plug structure that seats within the driver socket of the shell to rotationally lock the bushing relative to the shell.

21. The acetabular implant of claim 20, further comprising:
at least one threaded cap, wherein the shell includes at least one threaded hole extending between the interior and exterior surfaces, and the threaded cap is removably engaged within the threaded hole.

22. The acetabular implant of claim 21, wherein:
the threaded cap provides a seal between the interior and exterior surfaces.

23. The acetabular implant of claim 21, wherein:
the threaded cap has a tip that extends beyond from the exterior surface of the acetabular socket.

24. The acetabular implant of claim 23, wherein:
the tip has a conical shape.

25. The acetabular implant of claim 20, further comprising:
a structure extending around the open end of the shell to prevent debris material from entering between the exterior surface of the shell and the acetabulum when the acetabular implant is implanted at the hip joint.

26. The acetabular implant of claim 25, wherein:
the structure is a peripheral lip.

27. The acetabular implant of claim 26, wherein:
the lip includes teeth adapted to contact bone at or adjacent the acetabulum.

28. The acetabular implant of claim 20, wherein:
the bushing is made from ultra high molecular weight polyethylene (UHMWPe).

29. The acetabular implant of claim 20, wherein:
the reamer comprises a plurality of cutters.

30. The acetabular implant of claim 29, wherein:
the cutters are arranged in a plurality of rows.

31. The acetabular implant of claim 30, wherein:
the cutters comprise teeth.

32. A femoral implant for a prosthetic hip system for repair of a hip joint having a femur with a femoral head, including:
a) a cutter cap having a plurality of sides forming a polygonal periphery, an open end, and a partially closed end, the sides at the open end being sharp to define bone cutters that under force are adapted to cut the femoral head of the femur along the sides of the femoral head into a rotationally asymmetric shape, and the partially closed end including a hole adapting the cutter cap to receive a shaft there through; and
b) a femoral head cover having an outer surface with a spherical curvature, an inner opening sized and shaped to be stably received over the cutter cap in a rotationally fixed engagement.

33. The femoral implant of claim 32, wherein:
the sides of the cutter cap together define a square cross-sectional profile.

34. The femoral implant of claim 32, wherein:
at least one of the sides of the cutter cap is perforate, such perforation sized to permit bone ingrowth therein.

35. The femoral implant of claim 32, wherein:
the inner opening and the cutter cap have like cross-sectional shapes.

36. The femoral implant of claim 32, wherein:
the shaft is non-threaded at a central portion between the proximal and distal ends.

37. The femoral implant of claim 32, further comprising:
a coupling screw that that engages the femoral head cover and retains the femoral head cover over the cutter cap and to the femur.

38. The femoral implant of claim 37, wherein:
the femoral head cover includes a threaded screw hole axially positioned between the inner opening and the outer surface, and
the coupling screw has a head and a shaft, the shaft threaded at its proximal end with bone engaging threads, and threaded at its distal end with machine threads sized to threadedly engage the threaded screw hole of the femoral head cover.

39. The femoral implant of claim 38, wherein:
the bone engagement threads have a major diameter greater than a diameter of the central portion, and a minor diameter equal to the diameter of the central portion, and
the machine threads have a major diameter equal to the diameter of the central portion, and a minor diameter small than the diameter of the central portion.

* * * * *